United States Patent [19]
Fellmann et al.

[11] Patent Number: 5,268,523
[45] Date of Patent: Dec. 7, 1993

[54] SELECTIVE SORPTION OF DIALKYLATED MULTINUCLEAR AROMATIC COMPOUNDS

[75] Inventors: Jere D. Fellmann, Livermore; Paul R. Wentrcek, Redwood City; Peter H. Kilner, Sunnyvale, all of Calif.

[73] Assignee: Catalytica, Inc., Mountain View, Calif.

[21] Appl. No.: 659,416

[22] PCT Filed: Jul. 24, 1990

[86] PCT No.: PCT/US90/04153

§ 371 Date: Jan. 23, 1992

§ 102(e) Date: Jan. 23, 1992

Related U.S. Application Data

[63] Continuation-in-part of Ser. No. 384,647, Jul. 24, 1989, Pat. No. 5,017,735.

[51] Int. Cl.$^5$ .......................... C07C 2/64; C07C 2/68; C07C 7/12
[52] U.S. Cl. .................................. 585/446; 585/467; 585/820; 585/828; 585/831
[58] Field of Search ............... 585/820, 828, 831, 446, 585/467

[56] References Cited

U.S. PATENT DOCUMENTS

| | | | |
|---|---|---|---|
| 4,440,871 | 4/1984 | Lok et al. | |
| 4,567,029 | 1/1986 | Wilson et al. | |
| 5,001,295 | 3/1991 | Augevine et al. | 585/467 |
| 5,003,122 | 3/1991 | Fellman et al. | 585/467 |
| 5,015,797 | 5/1991 | Lee et al. | 585/467 |
| 5,017,735 | 5/1991 | Fellmann et al. | 585/820 |

FOREIGN PATENT DOCUMENTS 1-249729 5/1989 Japan .
2199590 7/1888 United Kingdom .

OTHER PUBLICATIONS

Broughton, D. B., "Bulk separations via absorption" CEP (Oct. 1977) pp. 49–51.
Meier et al., "Atlas of zeolite structure types" Second Edition, (1987) Butterworths Publishers, London, pp. 62–63.
Scherzer, J., "The Preparation and characterization of aluminum-deficient zeolites" Whyte et al., eds., *Catalytic Materials: Relationship Between Structure and Reactivity*, American Chemical Society, Washington, D.C., (1984) pp. 157–159.
Flanigen et al., "Aluminophosphate molecular sieves and the periodic table" Murakami et al., eds., *New Developments in Zeolite Science and Technology*, Elsevier, Amsterdam, (1986) pp. 103–112.
Derouane et al., "Diffusion and shape-selective catalysts in zeolites" Whittingham et al., eds., *Intercalation Chemistry*, Academic Press, New York, (1982) pp. 112–115.
Ernst et al., "Synthesis of zeolite ZSM-12 in the system $(MTEA)_2O-Na_2O-SiO_2-Al_2O_3-H_2O$" *Zeolites (1987) 7:458–462*.
Philippaerts et al., "The implantation of boron-nitrogen compounds in mordenite LP and their influence on the adsorption properties" *Stud. Surf. Sci. Catal.* (1986) 28:319–327.
Niwa et al., "Fine control of the pore-opening size of the zeolite mordenite by chemical vapor deposition of silicon alkoxide" *J. Chem. Soc. Faraday Trans.* (1984) 80:3135–3145.
Niwa et al., "Modification of H-mordenite by a vapour-phase deposition method" *J. Chem. Soc., Chem., Commun.* (1982) pp. 819–820.
Hidalgo et al., "Modification of mordenite by chemical vapour deposition of metal chloride" *Zeolites* (1984) 4:175–180.

*Primary Examiner*—Anthony McFarlane
*Assistant Examiner*—Nhat D. Phan
*Attorney, Agent, or Firm*—Morrison & Foerster

[57] ABSTRACT

The invention relates to a process for the separation of various dialkyl multinuclear aromatic compounds from a feed stream of mixed isomers of those compounds. A shape selective adsorbent is employed resulting in a process that is more efficient than processes based upon prior separation techniques. Of special interest are combination processes involving synthesis steps followed by sorption steps using the same shape selective materials.

8 Claims, 1 Drawing Sheet

SELECTIVE SORPTION OF DIALKYLATED MULTINUCLEAR AROMATIC COMPOUNDS

This is a continuation-in-part of U.S. Ser. No. 07/384,647 filed Jul. 24, 1989, and now U.S. Pat. No. 5,017,735.

FIELD OF THE INVENTION

The invention relates to a process for the separation of various dialkyl multinuclear aromatic compounds from a feed stream of mixed isomers of those compounds. A shape selective adsorbent is employed resulting in a process that is more efficient than processes based upon prior separation techniques. Of special interest are combination processes involving synthesis steps followed by sorption steps using the same shape selective materials.

BACKGROUND OF THE INVENTION

The present invention relates to a process for separating various dialkyl multinuclear aromatic compounds from streams containing their isomers. These isomers are of interest for the production of certain di-substituted aromatics which in turn are employed in the synthesis of liquid crystal polymers and specially polyesters.

The p,p'-dialkyl multinuclear aromatic products most suitable for this process, their respective stream, and shape selective catalysts are outlined in the table below:

| Product | Stream | Shape Selective Material |
| --- | --- | --- |
| 2,6-diisopropylbiphenyl (DIPN) | Mixed DIPN's | Mordenite |
| 4,4'-diisopropylbiphenyl (DIPBP) | Mixed DIBP's | ZSM-12, mordenite |
| 2,6-dimethylnaphthalene (DMN) | Mixed DMN's | ZSM-5 |
| 4,4-diethylbiphenyl | Mixed DEBP's | ZSM-12 |
| 2-methyl-6-isopropyl naphthalene (MIPN) | Mixed MIPN's | Mordenite |

Those liquid crystal polymers and specially polyesters would likely be commercially attractive if either dihydroxy or dicarboxy forms of the dialkyl multinuclear aromatic compounds were readily available. Unfortunately, they are not. Viable feedstocks which are convertible into either the dihydroxy or dicarboxy monomers based upon known technology are the compounds listed above.

In manufacturing these dialkyl multinuclear aromatics it is clear that some monoalkyl and trialkyl products and a mix of dialkyl isomers will also be produced. In any crude diethyl multinuclear aromatic product stream, separation of these isomers by thermal distillation is difficult because the boiling points of the respective isomers are very close. Similarly, isomer separation by fractional crystallization using melting points is inefficient and suffers from yield problems because of the loss of the desired product in the mother liquor and because of large recycle streams.

It is taught in U.K. Patent Application No. 2,199,590 filed Nov. 27, 1987, that a specific isomer of dimethylnaphthalene can be separated from other isomers when a zeolite Y containing specific metallic ions is used as an adsorbent in combination with a specific desorbent.

Similarly, the separation 4,4'-dialkylbiphenyls in using mordenites is suggested in Japanese Kokai 89/249,729 (assigned to Nippon Steel Chemical Co.).

The references do not suggest combination processes in which the shape selective material used to synthesize the desired p,p'-dialkyl multinuclear aromatic product in a first step is also -used to separate that product from its accompanying isomers.

SUMMARY OF THE INVENTION

Figure 1:
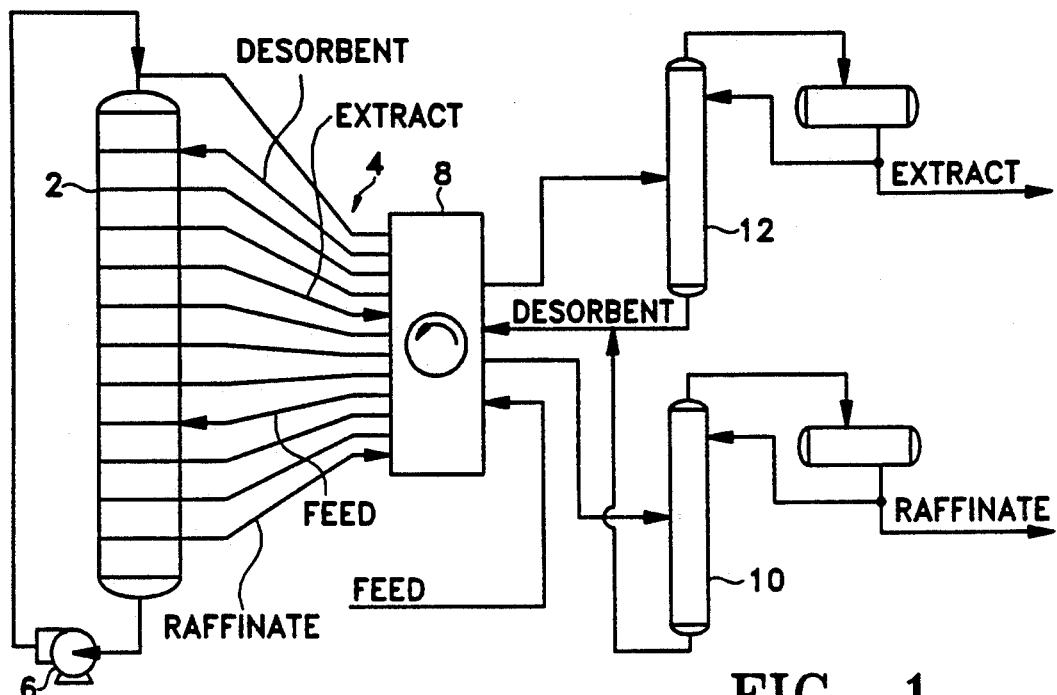
FIG. 1 represents a simulated moving bed column which can be employed in practicing the separation step of the present invention.

This invention is to an adsorbent process for the separation of p,p'-dialkyl multinuclear aromatic compounds from their isomers and, optionally, containing a synthesis step for producing those compounds using materials comprising the same shape selective materials.

Generically, the combination process entails synthesizing the p,p'-dialkyl multinuclear aromatic product compounds using feedstocks and acidic shape selective materials listed in the table below and then adsorbing those product compounds using the same shape selective materials.

| Products | Alkylating Agents | Aromatic Substrate | Shape Selective Material |
| --- | --- | --- | --- |
| 2,6-DIPN | Propylene, propanol, propyl chloride | Naphthalene, 2-isopropylnaphthalene | Mordenite |
| 2,6-DEN | Ethylene, ethanol, ethyl chloride | Naphthalene, 2-ethylnaphthalene | ZSM-12 |
| 4,4'-DIPBP | Propylene, propanol, propyl chloride | 4-isopropylbiphenyl, biphenyl | ZSM-12, mordenite |
| 2,6-DMN | Methanol, methyl chloride | Naphthalene, 2-ethylnaphthalene | ZSM-5 |
| 4,4'-DEBP | Ethylene, ethanol, ethyl chloride | 4-ethyl biphenyl, biphenyl | ZSM-12 |
| MIPN | Propylene, propanol, propyl chloride | Naphthalene, methyl naphthalene | Mordenite |

Particularly desirable is a process for the selective adsorption of 2,6-DIPN from a stream of DIPN's. The optimum shape selective adsorbent for DIPN separation is a class of crystalline molecular sieves all of which are characterized as having 12 member oxygen rings and pore aperture dimensions between approximately 5.5 Å and 7.0 Å, preferably mordenite.

Following the synthesis step (where used) and the adsorption step, the material held up in the interstices is removed. At this point, the bed of shape selective adsorbent contains sorbed material that is rich in p,p'-dialkyl multinuclear aromatic product. The product sorbed by the bed is then displaced from the bed with a suitable desorbent. The desorbent can then be separated from the desorbed product and recycled. If desired, this enriched material can be further purified by any of several means including, for example, distillation, crystallization, or a second absorption step.

DETAILED DESCRIPTION OF THE INVENTION

This invention is a process for, optionally, synthesizing p,p'-dialkyl multinuclear aromatic compounds and separating those compounds from other materials in the product stream. The catalyst used in the synthesis step and the adsorbent used in the separation step comprise, for a particular dialkyl multinuclear product, the same shape selective material.

The synthesis step generally takes place in the liquid phase in a convenient reactor. The reactor may be batch but preferable is continuous in nature. The alkylating agent is contacted with the polynuclear aromatic feedstock in the presence of the shape selective material. The reaction is conducted at an alkylating agent-/aromatic feedstock ratio between 0.1 and 10, preferably between 1.0 and 2.0 and at elevated temperatures and pressures, generally between 100° C. and 400° C., preferably between 250° C. and 350° C., and between 1 and 100 atmospheres, preferably 1 to 10 atmospheres. Under appropriate operating conditions, a larger amount of the noted p,p'-dialkyl multinuclear aromatic product will be produced than would be made using a non-selective acid catalyst such as silica-alumina. The products, alkylating agents, aromatic substrates and appropriate catalytic shape selective materials are specified in the table below:

| Products | Alkylating Agents | Aromatic Substrate | Shape Selective Material |
|---|---|---|---|
| 2,6-DIPN | Propylene, propanol, propyl chloride | Naphthalene, 2-isopropyl-naphthalene | Mordenite |
| 2,6-DEN | Ethylene, ethanol, ethyl chloride | Naphthalene, 2-ethylnaphthalene | ZSM-12 |
| 4,4'-DIPBP | Propylene, propanol, propyl chloride | 4,-isopropyl-biphenyl, biphenyl | ZSM-12, mordenite |
| 2,6-DMN | Methanol, methyl chloride | Naphthalene, 2-ethylnaphthalene | ZSM-5 |
| 4,4'-DEBP | Ethylene, ethanol, ethyl chloride | 4-ethyl biphenyl, biphenyl | ZSM-12 |
| MIPN | Propylene, propanol, propyl chloride | Naphthalene, methyl naphthalene | Mordenite |

The product stream, preferably containing enhanced or more than equilibrium amounts of the dialkylated aromatic product, may then be passed to a separation step. The separation step is typically performed in the liquid phase in a batch or simulated batch mode. The product stream containing dialkylates which are not p,p', and other alkylates such as monoalkylates and trialkylates, is contacted with an amount of the appropriate shape selective material. A minimal amount of experimentation to optimize the ratio of feedstock to shape selective material and similar operating conditions may be desirable. The mass of shape selective material is removed from contact with the stream and placed in contact with a desorbent stream. The p,p-dialkyl multinuclear aromatic compound which has been adsorbed into the pores of the shape selective material is desorbed by contact with an appropriate desorbent. That material comprises the same shape selective material as was used to synthesize the dialkyl aromatic product. The cation found in the shape selective material used in the separation step may be the same or different from that found in the synthesis step's material. The desorbents act with various levels of efficacy in removing the p,p'-dialkyl aromatic from the shape selective materials. Suitable desorbents should be easily separable (by distillation or otherwise) from the dialkyl aromatic and include $C_1$–$C_4$ ethers, single ring alkyl aromatics, and benzene. Particularly preferred desorbents are m-xylene, toluene, ethylbenzene, n-propylbenzene, isopropylbenzene, 4-ethyl toluene, and p-diethylbenzene.

The desorbent and p,p'-dialkyl multinuclear aromatic product are then separated as was noted above.

A particularly desirable aspect of the invention is the isolated step for the selective adsorption of 2,6-diisopropylnaphthalene from a feed stream of mixed diisopropylnaphthalenes as well as to a process for separating the 2,6-diisopropyl isomer from a mixture of isomers of diisopropylnaphthalenes. This may be done as a batch process while establishing a unit operation by moving the feed stream of mixed isomers over a bed of suitable adsorbent.

The present process can be carried out employing, for example, chemical processing equipment used for liquid bulk separations. For example, FIG. 1 illustrates a schematic representation of such bulk separation equipment as employed by UOP for the adsorptive separation of p-dialkylbenzene from other dialkylbenzene isomers. See D. B. Broughton, "Bulk Separations Via Adsorptions", Chemical Engineering Progress, pp. 49–51 (October, 1977). However, it must be emphasized that virtually any well known packed column can be employed insuring a flow of liquid feed stock and desorbent over a fixed bed of adsorbent which can be employed as a powder, pellet, or extrudate.

Referring to FIG. 1, the preferred process utilizes a column 2 filled with a fixed bed of adsorbent. The column has numerous ports 4 for feeding dialkylnaphthalene feed and desorbent as well as removing raffinate and extract. These ports are all piped to a rotary valve 8 which controls where in the adsorption column materials are fed and withdrawn. For a period of time, dialkylnaphthalene feed is provided to a section of the adsorption column wherein the adsorbent selectively adsorbs the desired 2,6-diisopropylnaphthalene isomer. The raffinate now depleted in the desired 2,6-diisopropylnaphthalene isomer is either recycled by pump 6 or withdrawn and sent to a column 10 where any desorbent it picks up is separated and returned. At a later period in time, the rotary valve 8 redirects the stream and now desorbent is fed over the portion of the packed bed which had previously adsorbed the desired 2,6-diisopropylnaphthalene isomer. The desorbent releases the desired isomer (the extract) from the adsorbent and passes through the rotary valve to a column 12 in which 2,6-diisopropylnaphthalene is separated from the desorbent.

Such a process may also be used to separate the other dialkyl aromatic products from their isomers.

If the 2,6-diisopropylnaphthalene enriched product does not contain sufficient purity of the desired isomer, it clan be further purified by another adsorption step, fractional crystallization, or other conventional separation means.

The adsorbents employed for the preferential removal of the 2,6-diisopropyl isomer from a feed stock of mixed dialkylated naphthalenes are one or more crystalline molecular sieves such as those taught in applicants' copending U.S. application Ser. No. 254,284, filed on Oct. 5, 1988, entitled SELECTIVE ISOPROPYLATION OF NAPHTHALENES TO 2,6-DIISO- PROPYLNAPHTHALENE, the disclosure of which is hereby incorporated by reference. Broadly, the adsorbents of the present invention for the selective adsorption of 2,6-diisopropylnaphthalene from other diisopropylnaphthalene isomers are crystalline molecular sieves containing 12 membered oxygen rings and pore aperture dimensions between approximately 5.5 Å and 7.0 Å.

Shape selective adsorption occurs when the zeolite framework and its pore structure allow molecules of a given size and shape to preferentially diffuse into and adsorb within the intracrystalline free space. It is therefore important to characterize accurately the pore structure that is encountered in the various crystalline molecular sieve frameworks. Pore structure (dimensions and network) varies greatly among zeolites. Without modifications of the zeolite structure, the lowest pore aperture dimension is about 2.6 Å and the highest is 7.4 Å. Maximum values for the four-, six-, eight-, ten-, and twelve-membered oxygen rings have been calculated to be 2.6 Å, 3.6 Å, 4.2 Å, 6.3 Å, and 7.4 Å, respectively. Pores may lead to linear, parallel, or interconnected channels or may give access to larger intracrystalline cavities, sometimes referred to as cages. For all zeolites, the pore opening is determined by the free aperture of the oxygen ring that limits the pore aperture.

The free diameter values given in the channel description and on the ring drawings (not shown here) are based upon the atomic coordinates of the type species in the hydrated state and an oxygen radius of 1.35 Å, as determined from x-ray crystallographic data. Both minimum and maximum values are given for noncircular apertures. In some instances, the corresponding interatomic distance vectors are only approximately coplanar; in other cases the plane of the ring is not normal to the direction of the channel. Close inspection of the framework and ring drawings should provide qualitative evidence of these factors. Some ring openings are defined by a very complex arrangement of oxygen atoms. Included are references to publications which contain extensive drawings and characterization data. The relevant portions of those references are incorporated herein. It should be noted that crystallographic free diameters may depend upon the hydration state of the zeolite particularly for the more flexible frameworks. It should also be borne in mind that effective free diameters can be temperature dependent.

As used throughout the instant specification, the term "pore aperture" is intended to refer to both the pore mouth at the external surface of the crystalline structure, and to the intracrystalline channel, exclusive of cages. When a crystalline molecular sieve is hereinafter characterized by a "pore aperture dimension," adopted is the geometric dimensional analysis defined as "crystallographic free diameter of channels" in Meier, W. M., Olson, D. H., *Atlas of Zeolite Structure Types*, (Butterworth's, 1987, 2d Rev. Ed.). The term "dimension" is preferred over "diameter" because the latter term implies a circular opening, which is not always accurate in crystalline molecular sieves.

Crystalline molecular sieves which are useful in practicing the present process include MeAPSO-46, offretite, ZSM-12 and synthetic mordenite. Preferred adsorbents are synthetic mordenite, with pore aperture dimensions of 6.5 Å and 7.0 Å and ZSM-12 with pore aperture dimensions of 6.2 Å, 5.7 Å and 5.5 Å. These preferred adsorbents can be used in the adsorption process without any pretreatment to modify their pore aperture dimensions. Synthetic mordenite is particularly preferred while other useful adsorbents may be obtained by treatment of a crystalline molecular sieve having pore aperture dimensions greater than 7.0 Å selected from the group consisting of zeolite L, zeolite Beta, faujasite and SAPO-5 to reduce the dimensions of the pore apertures. Mordenite, ZSM-12, off retite and MeASPO-46 fall into the first class of adsorbents whose pore aperture dimensions are between 5.5 Å and 7.0 Å, prior to any modification to their pores.

The preferred adsorbents, mordenite and ZSM-12, as well as other suitable sieves, can be optimized to greater selective adsorption of the desired 2,6-diisopropylnaphthalene without substantially altering their pore dimensions by modifying the hydrophobic character of the molecular sieves. One such modification to the preferred adsorbents is to dealuminate. Dealumination of acidic crystalline molecular sieve materials can be achieved by exposing the molecular sieve to mineral acids such as HCl. The desired degree of dealumination will dictate the strength of acid used and the time during which the crystalline structure is exposed to the acid. It is also common to use a steam treatment in combination with the acid leach to dealuminate the zeolite materials. For additional methods of preparing aluminum-deficient zeolites, see J. Scherzer, "The Preparation and Characterization of Aluminum-Deficient Zeolites", Thaddeus E. Whyte et al., "Catalytic Materials: Relationship Between Structure and Reactivity", ACS Symposium Series 248, pp. 156-60 (American Chemical Society, 1984). Dealumination according to the instant invention is intended to achieve a Si:Al ratio above 3 and preferably above 15. Dealumination can also be applied to the second class of molecular sieve materials whose pore aperture dimensions exceed 7.0 Å.

A dealuminated crystalline molecular sieve can be calcined at temperatures between 400° C. and 1000° C., preferably between 400° C. and 600° C. Calcination serves to dehydrate or "heal" Si—OH bonds or "nests" after dealumination. Healing these nests provides for a more uniform pore structure within the crystalline material, leading to structural stability and ultimately resulting in improved adsorption. For a zeolite like hydrogen mordenite, the optimal temperature range was found experimentally to lie between 400° C. and 600° C., but preferentially at 500° C. See Mathur, Kuldeep, Narain, Ph.D. Thesis, University of Pittsburgh, 1977. In the case of H-mordenite, removal of extra and intra crystalline water can be accomplished effectively in the presence of an atmosphere of oxygen or nitrogen. As previously noted, other adsorbents may also be considered which have aperture dimensions in excess of 7.0 Å. These other adsorbents are obtained by a combination of modifications of commercially available, acidic crystalline molecular sieve products. Examples of such sieves include zeolite L, zeolite Beta, faujasite and SAPO-5, which have 12 membered oxygen rings whose pore aperture dimensions typically exceed 7.0 Å. SAPO is an acronym for silicoaluminophosphate molecular sieves, first reported in 1984. See B. M. Lok et al U.S. Pat. No. 4,440,871. MeAPO is an acronym for metalaluminophosphate molecular sieves reported in S. T. Wilson et al U.S. Pat. No. 4,567,029. For more complete characterizations of each of the catalyst members discussed above, see Flanigen, E. M., et al., *Stud. Surf. Sci. Cat.*, 28, pp. 103-12. Also, see E. G. Derouane, "Diffusion and Shape-Selective Catalysis in Zeolites",

*Intercalation Chemistry*, pp. 112-14, Ed. by M. Stanley Whittingham (Academy Press, 1982). Also, see S. Ernst, *Zeolites*, Vol. VII, p. 458 (1987), for a good discussion of ZSM-12.

When using adsorbents obtained by the treatment of crystalline molecular sieves whose pore aperture dimensions are initially above 7.0 Å, internal acid site modification can be used to reduce the pore aperture dimensions to an extent which show an enhanced 2,6-diisopropylnaphthalene selectivity. Molecular sieves with reduced pore aperture dimensions are best described with reference to their performance in the adsorption under consideration. Those crystalline molecular sieves which have been adequately modified by internal acid site treatment will perform the selective adsorption of 2,6-diisopropylnaphthalene.

Ion exchange can be used to treat crystalline molecular sieves whose pore aperture dimensions are initially above 7.0 Å and reduce the pore aperture to the desired range. Elements suitable for ion exchange include alkali metals and alkali earth metals.

Crystalline molecular sieves may be treated to modify internal acid sites by contact with reagents selected from the group consisting of halogen, hydridic and organic derivatives of group 3A, 4A, 4B and 5A. Preferred embodiments of the internal acid site reagents include $B_2H_6$, $SiH_4$ and $PH_3$. For a more complete discussion of the internal acid site modification techniques contemplated herein, see A. Thijs et al., *J. Chem. Soc. Faraday Trans.*, 79, 2821 (1983). See also J. Philippaerts et al., "The Implantation of Boron-Nitrogen Compounds in Mordenite LP and Their Influence on the Adsorption Properties", *Stud. Surf. Sci. Catal.*, 28, pp. 305-10 (1986). The relevant portions of each of these citations are incorporated herein by reference.

In addition to the use of the above described reagents which tend to be nonspecific, there is an intermediate level of crystalline molecular sieve modification which can be used to perform "pore mouth engineering". These reagents provide an intermediate level since they are not specific for external acid site, but are not entirely nonspecific, leading to substantial internal acid site modification. In selecting an intermediate reagent, the characteristics and pore aperture dimensions of the starting crystalline molecular sieve must be matched against the molecular dimensions of the reagent.

It has been shown that chemical vapor deposition of $Si(OCH_3)_4$ on H-mordenite can be successfully used to control the intracrystalline pore aperture without substantially affecting the adsorbent's internal surface acid properties. $Si(OCH_3)_4$ can be deposited irreversibly on zeolite without entering the intracrystalline pores. See Niwa, M. et al., *J. Chem. Soc., Faraday Trans.*, 1, 1984, 80, pp. 3135-45; Niwa, M. et al., "Modification of H-Mordenite by Vapor-Phase Deposition Method", *J. Chem. Soc. Commun.*, p. 819-20 (1982).

Similarly, chemical vapor deposition of metal chlorides such as $SiCl_4$, $GeCl_4$, $TiCl_4$, and $SnCl_4$ can be effective to modify pore mouth structures. These metal molecules with a range of molecular dimensions can be selected to be larger than the adsorbent pore aperture, thereby preventing substantial diffusion into the internal pore. See Hidalgo, T. V. et al., *Zeolites*, 4, pp. 175-80 (April, 1984).

The pore-modifying agents can be contacted with the molecular sieves in either solution or in vapor phase.

As noted previously, the crystalline molecular sieve adsorbent can be supplied as a powder, pellet or extrudate. Pellets and extrudates can be made according to known techniques for binding powder. Pellets can be formed by applying pressure to powder. Pellets and extrudates can be formed by using binders such as alumina, clays, silica, or can be silica-alumina as well known in the art. In one embodiment of the process, the adsorbent is packed in a column and a stream of mixed diisopropylnaphthenes pass through the column. After a suitable contact time with the adsorbent bed, the depleted dialkylnaphthalene stream is purged from the packed bed. In a second step, a desorbent is fed to the column to remove the adsorbed isomers. The stream containing the desorbent and the adsorbed isomers is collected. The dialkylate fraction of this stream which is enriched in 2,6-diisopropylnaphthalene, can be separated from the desorbent by any conventional separation means such as by crystallization, thermal distillation or chromatographic adsorption. It is also contemplated that a series of adsorption/desorption cycles can be employed.

The desorbent is a liquid chosen to desorb selectively the isomers absorbed by the adsorbent. The desorbent is also chosen as a material which is easily and efficiently separated from the desired 2,6-diisopropyl isomer. In this regard, it was found that various alcohols, ethers, single ring alkyl aromatics such as p-xylene and o-xylene are particularly preferred while other desorbents contemplated for use herein include m-xylene, toluene, ethylbenzene, n-propylbenzene, isopropylbenzene, 4-ethyltoluene, 1,2,4-trimethylbenzene, p-diethylbenzene, p-cymene, 1,2,3,4-tetrahydronaphthalene and mixtures thereof.

The temperature and pressure conditions for the adsorption process also affect the diffusion rate. The temperature must be between ambient and 300° C., preferably between 100° C. and 200° C. The pressure in the packed column must be between 0 psia and 5000 psia, preferably about atmospheric pressure but in any case higher than the vapor pressure of the alkylnaphthalene feed at the temperature of the adsorption step.

EXAMPLES

Example 1

A ¼ inch O.D. stainless steel tube 12 inches long was packed with a steam de-aluminated, acid washed and calcined mordenite powder (381-10, Si/Al 32 23). The column was heated to a temperature of 104°–119° C. and a sample of a dialkylnaphthalene stream was pumped over the bed at a rate of 0.25 ml/min. Analysis of the initial liquid exiting the column showed a depletion of 2,6-diisopropylnaphthalene isomer over that contained in the feed stream (Table 1).

TABLE 1

| Total Isomer/DIPN's | Initial Ratio (% by Wt.) | Final Ratio (% by Wt.) |
|---|---|---|
| 2,6 | 18.8 | 4.9 |
| 2,7 | 15.8 | 10.7 |
| 1,3 | 20.6 | 30.1 |
| 1,5 | 4.0 | 3.8 |
| 1,4 | 8.1 | 11.3 |
| 1,6 | 17.0 | 24.3 |
| 1,7 | 14.2 | 12.8 |
| Total | 98.5 | 97.9 |
| 2,6/2,7-DIPN | 1.2 | 0.5 |

These data show that the 2,6-diisopropylnaphthalene isomer was preferentially removed from the dialkylnaphthalene stream since the 2,6/2,7 ratio dropped from 1.2 to 0.5. Also the percentage of the 2,6-diisopropyl isomer changed from 18.8 to 4.9% further illustrating the selection of this isomer by the adsorbent.

Example 2

The mordenite sieve used in Example 1 was loaded into a ¼ inch diameter stainless steel tube 12 inches long. A mixture of diisopropylnaphthalenes was pumped over ca. 1.8 gm of the sieve at 157° C. at 0.25 ml/min. Samples of the dialkylnaphthalenes passing over the mordenite bed were collected at 0.5 ml increments. Table 2 shows the mole % composition of the dialkylnaphthalene stream fed to the column. The initial 2,6/2,7 ratio was 1.19. Table 3 shows the 2,6/2,7 ratio for the samples collected after contact with the mordenite. The data shows that the 2,6/2,7 ratio dropped from 1.19 to 0.5 after 4.3 ml were pumped.

TABLE 2

| Mole % Composition of DIPN | |
| --- | --- |
| Isomer | mol % |
| 2,6 | 18.8 |
| 2,7 | 15.8 |
| 1,3 | 20.6 |
| 1,5 | 4.0 |
| 1,4 | 8.1 |
| 1,6 | 17.0 |
| 1,7 | 14.2 |

TABLE 3

| 2,6/2,7 Ratio of Adsorbed DIPN | |
| --- | --- |
| volume pumped (ml) | 2,6/2,7 |
| 4.3 | 0.50 |
| 5.0 | 1.13 |
| 7.0 | 1.17 |
| 9.5 | 1.19 |

After pumping 9.5 ml of dialkylnaphthalene, the 2,6/2,7 ratio finally reached the initial value.

Figure 2:
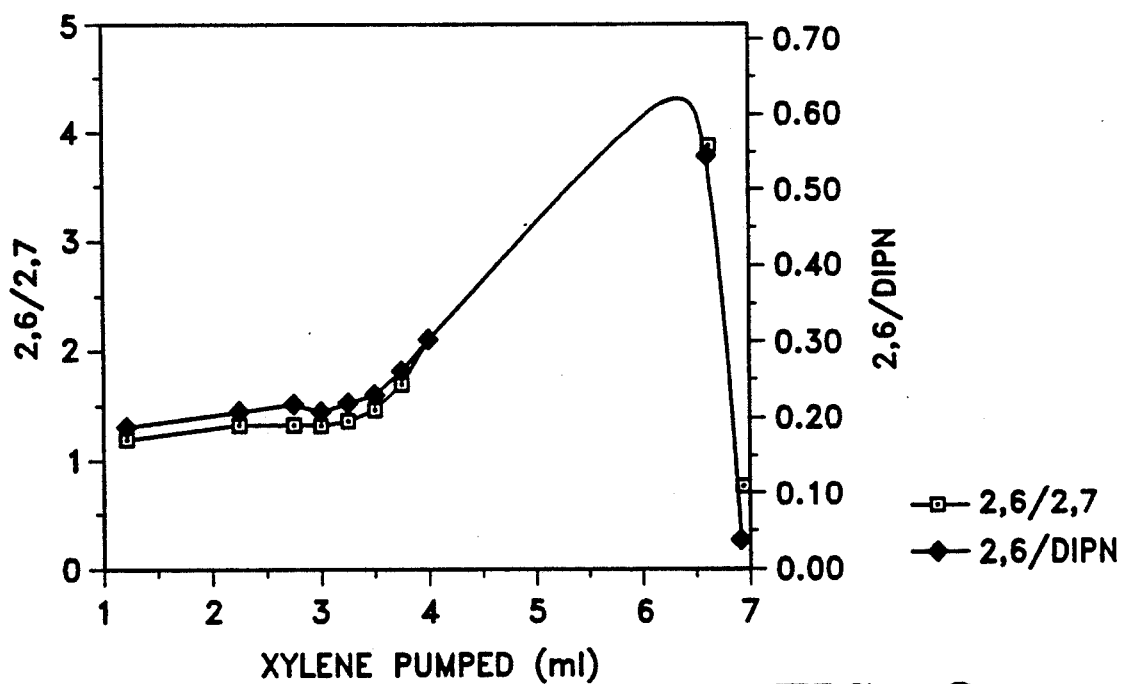
FIG. 2 is a graph demonstrating the efficacy of the present invention by comparing ratios of 2,6-diisopropylnaphthalene adsorbed with the volume of desorbent employed.

After the 2,6/2,7 ratio was at the initial value of 1.19 the dialkylnaphthalene feed stream was turned off and p-xylene was pumped to flush the adsorbed 2,6-diisopropylnaphthalene from the sieve. FIG. 2 shows the ratio of the 2,6-diisopropyl isomer/total dialkylated naphthalenes as a function of the amount of xylene pumped. From the graph it can be seen that the first material eluted is probably the original dialkylate displaced from the void space between the mordenite particles, since the 2,6/total isomers is 0.2 (or 20%) initially. The maximum in the curve is due to the 2,6-isomer being displaced from the pore of the sieve. The enrichment is significant since the sample taken at 6.8 ml contains 54% 2,6-DIPN as compared to 19% in the initial dialkylate mixture.

We claim as our invention:

1. A process for the production and separation of p,p'-dialkyl multinuclear aromatic compounds comprising the steps of:
   a. alkylating a multinuclear aromatic feedstock using an alkylating agent in the presence of a catalyst comprising a shape selective material selected from ZSM-12, ZSM-5, and mordenite to produce a synthesized alkylate stream containing a p,p'-dialkyl multinuclear aromatic product compound, and
   b. separating the p,p'-dialkyl multinuclear aromatic product compound from the synthesized alkylate stream by contacting that synthesized alkylate stream with an adsorbent comprising a member selected from ZSM-12, ZSM-5, and mordenite to adsorb the p,p'-dialkyl multinuclear aromatic product, wherein the adsorbent is comprised of the same material as used for the catalyst.

2. The process of claim 1 additionally including the step of desorbing the p,p'-dialkyl multinuclear aromatic product from the adsorbent.

3. The process of claim 2 where the p,p'-dialkyl multinuclear aromatic product is 2,6-diisopropylnaphthalene and the catalyst and the adsorbent each comprise mordenite.

4. The process of claim 2 where the p,p'-dialkyl multinuclear aromatic product is 2,6-diethylnaphthalene and the catalyst and the adsorbent each comprise ZSM-12.

5. The process of claim 2 where the p,p'-dialkyl multinuclear aromatic product is 4,4'-diisopropylbiphenyl and the catalyst and the adsorbent are selected from ZSM-12 and mordenite.

6. The process of claim 3 where the p,p'-dialkyl multinuclear aromatic product is 2,6-dimethylnaphthalene and the catalyst and the adsorbent each comprise ZSM-5.

7. The process of claim 2 where the p,p'-dialkyl multinuclear aromatic product is 4,4'-diethylbiphenyl and the catalyst and the adsorbent each comprise ZSM-12.

8. The process of claim 2 where the p,p'-dialkyl multinuclear aromatic product is methylisopropyl naphthalene and the catalyst and the adsorbent each comprise mordenite.

* * * * *